United States Patent
Geldwert

(10) Patent No.: US 10,327,823 B2
(45) Date of Patent: Jun. 25, 2019

(54) SURGICAL IMPLANT FOR CORRECTION OF HALLUX VALGUS OR TAILOR'S BUNION

(71) Applicant: Josef J. Geldwert, New York, NY (US)

(72) Inventor: Josef J. Geldwert, New York, NY (US)

(*) Notice: Subject to any disclaimer, the term of this patent is extended or adjusted under 35 U.S.C. 154(b) by 612 days.

(21) Appl. No.: 14/391,886

(22) PCT Filed: Mar. 6, 2013

(86) PCT No.: PCT/US2013/029267
§ 371 (c)(1),
(2) Date: Oct. 10, 2014

(87) PCT Pub. No.: WO2013/154697
PCT Pub. Date: Oct. 17, 2013

(65) Prior Publication Data
US 2015/0119944 A1 Apr. 30, 2015

Related U.S. Application Data

(60) Provisional application No. 61/623,979, filed on Apr. 13, 2012, provisional application No. 61/623,443, filed on Apr. 12, 2012.

(51) Int. Cl.
*A61B 17/80* (2006.01)
*A61B 17/82* (2006.01)
(Continued)

(52) U.S. Cl.
CPC ...... *A61B 17/8061* (2013.01); *A61B 17/8004* (2013.01); *A61B 17/82* (2013.01); *A61B 2017/565* (2013.01); *A61B 2017/681* (2013.01)

(58) Field of Classification Search
CPC ............ A61B 17/8061; A61B 17/8076; A61B 17/8004; A61B 17/8019; A61B 17/82;
(Continued)

(56) References Cited

U.S. PATENT DOCUMENTS 3,824,995 A * 7/1974 Getscher ................ A61B 17/74
606/281
4,269,180 A * 5/1981 Dall .................... A61B 17/0642
606/281
(Continued)

FOREIGN PATENT DOCUMENTS

RU 2056801 3/1996
WO WO 2010/106507 A2 9/2010

OTHER PUBLICATIONS

Supplemental European Search Report for European Patent Application No. EP 13775253.1 dated Jan. 4, 2016.
(Continued)

*Primary Examiner* — Matthew J Lawson
*Assistant Examiner* — Amy R Sipp
(74) *Attorney, Agent, or Firm* — Heslin Rothenberg Farley & Mesiti P.C.

(57) ABSTRACT

Methods and devices for correcting hallux valgus and tailor's bunion are disclosed. An implant includes a bone engaging feature on each end connected by an intermediate portion. The implant is configured to be positioned on the dorsal side of the metatarsals and stabilizes two adjacent metatarsals toward one another, thereby decreasing the intermetatarsal angle. Depending on the severity of the deformity, a single or multiple implants may be used. In addition, the implant may be used as an adjunctive device in combination with other surgical procedures.

18 Claims, 17 Drawing Sheets

(51) Int. Cl.
*A61B 17/56* (2006.01)
*A61B 17/68* (2006.01)

(58) Field of Classification Search
CPC . A61B 17/823; A61B 17/826; A61B 17/7022; A61B 17/7056; A61B 17/7047; A61B 17/7062; A61B 2017/681; A61B 2017/565
See application file for complete search history.

(56) References Cited

U.S. PATENT DOCUMENTS

| | | | |
|---|---|---|---|
| 4,409,974 A | 10/1983 | Freedland | |
| 5,246,443 A * | 9/1993 | Mai | A61B 17/0642 606/219 |
| 5,529,075 A | 6/1996 | Clark | |
| 5,725,582 A | 3/1998 | Bevan et al. | |
| 6,051,007 A * | 4/2000 | Hogendijk | A61B 17/08 606/151 |
| 6,066,141 A * | 5/2000 | Dall | A61B 17/82 606/281 |
| 6,451,019 B1 | 9/2002 | Zucherman et al. | |
| 6,872,210 B2 | 3/2005 | Hearn | |
| 7,235,091 B2 | 6/2007 | Thornes | |
| 7,335,204 B2 * | 2/2008 | Tornier | A61B 17/8061 606/280 |
| 7,635,365 B2 | 12/2009 | Ellis et al. | |
| 7,875,058 B2 | 1/2011 | Holmes, Jr. | |
| 8,246,664 B2 | 8/2012 | Terrill et al. | |
| 8,257,403 B2 | 9/2012 | Den Hartog et al. | |
| 8,277,459 B2 | 10/2012 | Sand et al. | |
| 8,398,678 B2 | 3/2013 | Baker et al. | |
| 8,425,554 B2 | 4/2013 | Denove et al. | |
| 8,652,141 B2 | 2/2014 | Rush et al. | |
| 8,696,716 B2 | 4/2014 | Kartalian et al. | |
| 8,696,719 B2 | 4/2014 | Lofthouse et al. | |
| 2002/0143336 A1 | 10/2002 | Hearn | |
| 2004/0116930 A1 * | 6/2004 | O'Driscoll | A61B 17/8061 606/281 |
| 2005/0085819 A1 | 4/2005 | Ellis et al. | |
| 2008/0234679 A1 * | 9/2008 | Sarin | A61B 17/74 606/70 |
| 2009/0036893 A1 | 2/2009 | Kartalian et al. | |
| 2009/0210011 A1 | 8/2009 | Den Hartog et al. | |
| 2010/0152752 A1 | 6/2010 | Denove et al. | |
| 2010/0211071 A1 | 8/2010 | Lettmann et al. | |
| 2010/0217328 A1 | 8/2010 | Terrill et al. | |
| 2011/0077656 A1 | 3/2011 | Sand et al. | |
| 2011/0093018 A1 | 4/2011 | Prasad et al. | |
| 2011/0178552 A1 | 7/2011 | Biscup et al. | |
| 2011/0178557 A1 | 7/2011 | Rush et al. | |
| 2011/0224729 A1 | 9/2011 | Baker et al. | |
| 2011/0301648 A1 | 12/2011 | Lofthouse et al. | |
| 2012/0016426 A1 | 1/2012 | Robinson | |

OTHER PUBLICATIONS

International Search Report and Written Opinion for PCT/US13/29267, dated May 31, 2013 (9 pages).

* cited by examiner

SURGICAL IMPLANT FOR CORRECTION OF HALLUX VALGUS OR TAILOR'S BUNION

BACKGROUND

1. Field

Aspects herein relate to a surgical implant for correction of hallux valgus or tailor's bunion. Methods of correcting hallux valgus and tailor's bunion using a surgical implant are also described herein.

2. Discussion of Related Art

Hallux valgus, commonly known as a bunion, is a condition or deformity in which the big toe points toward the second toe, resulting in a protrusion at the metatarsophalangeal (MTP) joint of the first metatarsal.

Tailor's bunion, also known as a bunionette, is a similar condition or deformity in which the fifth toe points toward the fourth toe, resulting in a protrusion at the MTP joint of the fifth metatarsal.

Non-surgical treatment of hallux valgus includes externally applied devices such as orthotics, bunion pads, arch supports, and braces. Surgical procedures to correct bunions include arthroplasty, osteotomy, and arthrodesis. Conventional implantable devices include an artificial joint that replaces all or part of the MTP joint and a suture-button construct that passes through and between the first and second metatarsal bones to laterally tension the first metatarsal bone towards the second metatarsal bone.

SUMMARY OF INVENTION

The inventor has found that the use of conventional suture-button implants gives rise to a high incidence of complications, including loosening of knots, stress fractures, stress risers, and recurrence of hallux valgus and/or tailor's bunion. Suture-button constructs invasively pass through the metatarsal bones, which may contribute to these complications.

The inventor has appreciated that such complications may be reduced with the use of a less invasive implant that does not pass through the metatarsal bones. Accordingly, the implants described herein may at least partially wrap around the metatarsal bones rather than pass through them, and may be positioned on only the dorsal side of the metatarsal bones, enabling a less invasive and more comfortable arrangement.

According to one aspect, an implant for repositioning bones of a patient to a more anatomically correct position is provided. The implant includes a first bone engaging feature configured to wrap partially around the first bone, a second bone engaging feature configured to wrap partially around the second bone, and an intermediate portion connecting the first and second bone engaging features, the intermediate portion and the bone engaging features cooperating to enable the first bone to be drawn toward the second bone.

According to one aspect, a method of repositioning bones of a patient to a more anatomically correct position is provided. The method includes engaging a first bone engaging feature to a first bone such that the first bone engaging feature partially wraps around the first bone, engaging a second bone engaging feature to a second bone such that the second bone engaging feature partially wraps around the second bone, and drawing the first bone toward the second bone with an intermediate portion that connects the first and second bone engaging features.

According to another aspect, an implant for repositioning bones of the patient to a more anatomically correct position is provided. The implant includes a first bone engaging feature configured to engage a first bone, a second bone engaging feature configured to engage a second bone, an intermediate portion connecting the first and second bone engaging features, the intermediate portion and the bone engaging features cooperating to enable the first bone to be drawn toward the second bone, wherein the intermediate portion is arranged such that, when the implant is engaged with the first and second bones, the intermediate portion is located only dorsal to metatarsals of a foot of the patient.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which.

DETAILED DESCRIPTION

Hallux valgus and tailor's bunions have a wide variety of causes. Some deformities may be inherited or present at birth, while others are self-inflicted. Self-inflicted causes include high-heeled or ill-fitting shoes, high-impact exercise, foot injuries, and the like. As used herein, the top side of the foot will be referred to as the dorsal side and the bottom side of the foot will be referred to as ventral side or plantar side. Thus, a top facing surface of the implant may be referred to as the dorsal side and the bottom facing surface of the implant may be referred to as the plantar side or ventral side. In either case, as will be appreciated below, the implant in some embodiments will be positioned on the top side of the metatarsals such that the plantar side (or ventral side) of the implant faces the dorsal side of the metatarsals.

Figure 1B:
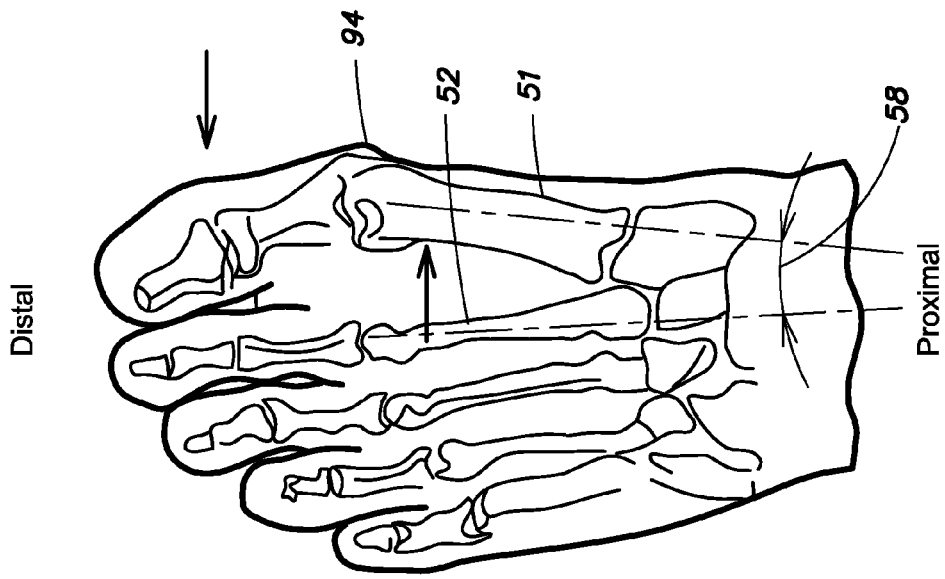
FIG. 1B depicts a foot exhibiting hallux valgus.
Figure 1A:
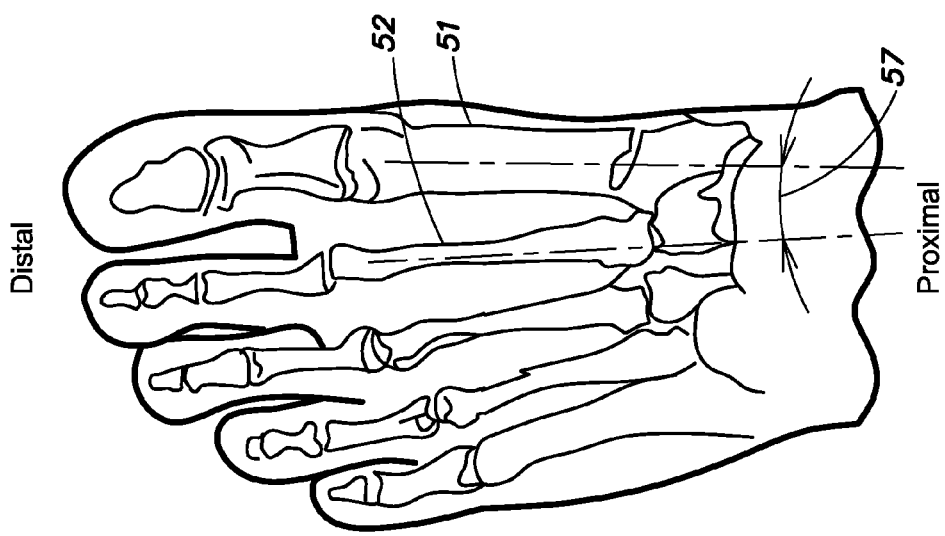
FIG. 1A depicts a healthy foot without hallux valgus.
Figure 2:
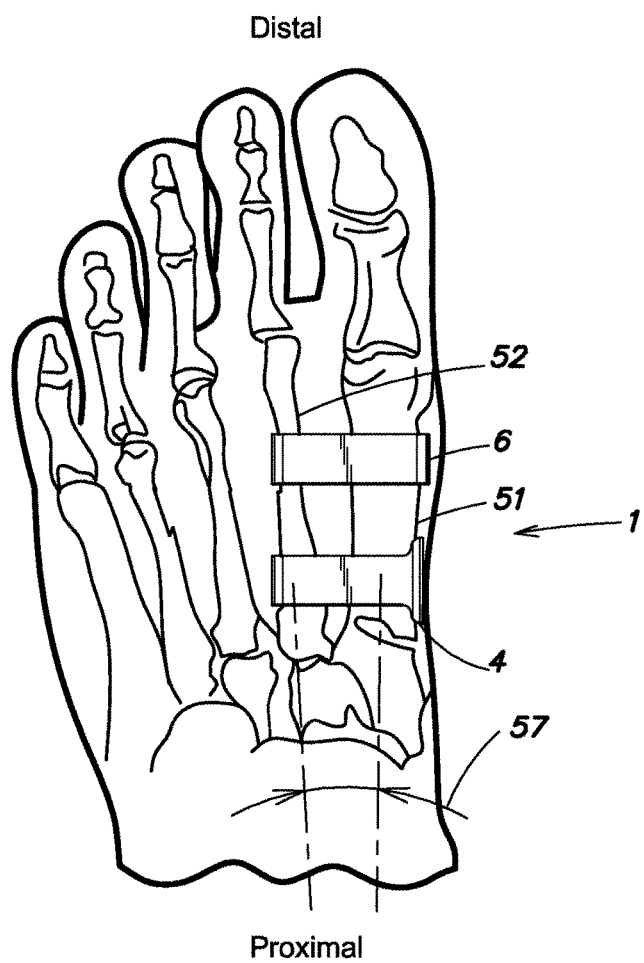
FIG. 2 depicts a corrected foot with an implant system positioned on the first and second metatarsals in accordance with an aspect of the invention.

FIG. 1A depicts a healthy foot while FIG. 1B depicts a foot exhibiting hallux valgus. Hallux valgus may develop when the pressures of bearing and shifting of weight fall unevenly on the joints and tendons in the feet. This imbalance and pressure makes the big toe joint unstable, leading to splaying of the first 51 and second 52 metatarsals, and resulting in a protrusion 94 at the MTP joint of the first metatarsal. As shown in FIG. 1A, in a normal foot, the intermetatarsal angle 57 between the first 51 and second 52 metatarsal bones is typically less than about 9 degrees. As shown in FIG. 1B, a foot exhibiting hallux valgus has an intermetatarsal angle 58 between the first 51 and second 52 metatarsal bones greater than that of a normal foot, ranging from about 9 to 20 degrees. As shown in FIG. 2, implant system 1, including proximal implant 4 and distal implant 6, may stabilize the first metatarsal 51 to the second metatarsal 52, resulting in a more anatomically correct intermetatarsal angle 57 resembling that of the healthy foot in FIG. 1A.

Figure 12B:
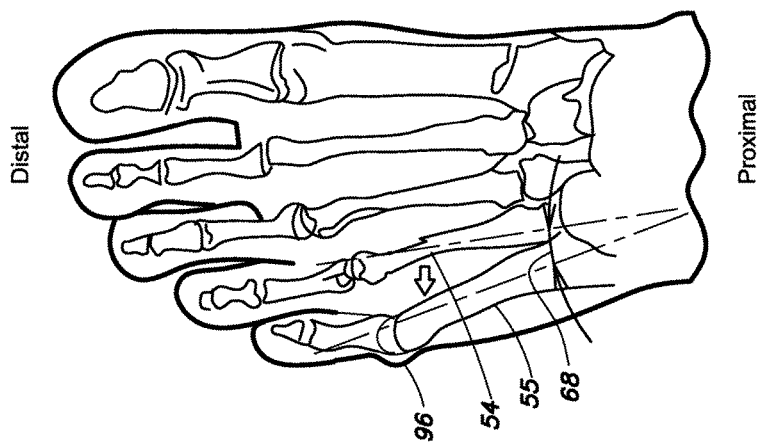
FIG. 12B depicts a foot exhibiting tailor's bunion.
Figure 12A:
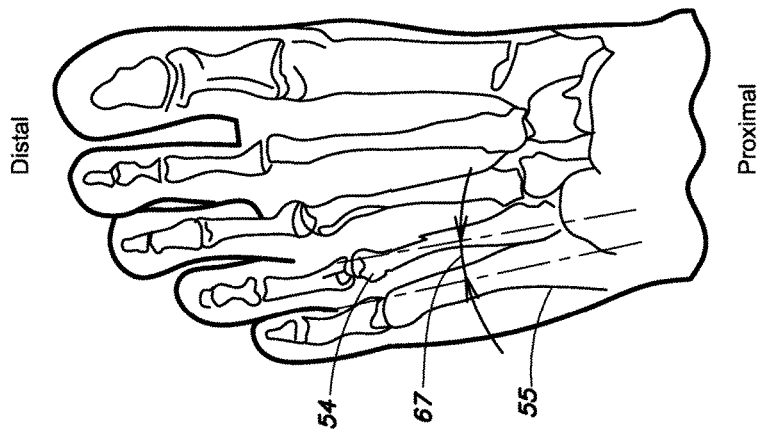
FIG. 12A depicts a healthy foot without tailor's bunion.

Similarly, tailor's bunion involves instability of the fifth metatarsal that leads to splaying of the fourth and fifth metatarsals. FIG. 12A depicts a healthy foot while FIG. 12B depicts a foot with tailor's bunion. With tailor's bunion, splaying of the fourth 54 and fifth 55 metatarsal results in a protrusion 96 at the MTP joint of the fifth metatarsal. As shown in FIG. 12A, in a normal foot, the intermetatarsal angle 67 between the fourth 54 and fifth 55 metatarsal bones is typically less than about 8 degrees. As shown in FIG. 12B, a foot with tailor's bunion has an intermetatarsal angle 68 between the fourth 54 and fifth 55 metatarsal bones greater than that of a normal foot, ranging from about 8 to 15 degrees.

One challenge with the use of surgical implants is attachment to the bones. Prior implants anchor to the foot bones by fully penetrating through the metatarsals and/or wrapping completely around the metatarsals. Arrangements that penetrate completely through the metatarsals are more invasive, as they may weaken the structural integrity of the bones and lead to stress fractures and stress risers. Arrangements that wrap completely around the metatarsals may require invasive surgical procedures, and may be bulky and uncomfortable to the patient.

According to one aspect of the invention, the surgical implant may partially wrap around the metatarsal bone rather than penetrate completely through the entire metatarsal bone, and may be positioned on only the dorsal side of the metatarsal bones, allowing the implant to engage the metatarsals while enabling a less invasive surgical procedure.

Figure 3A:
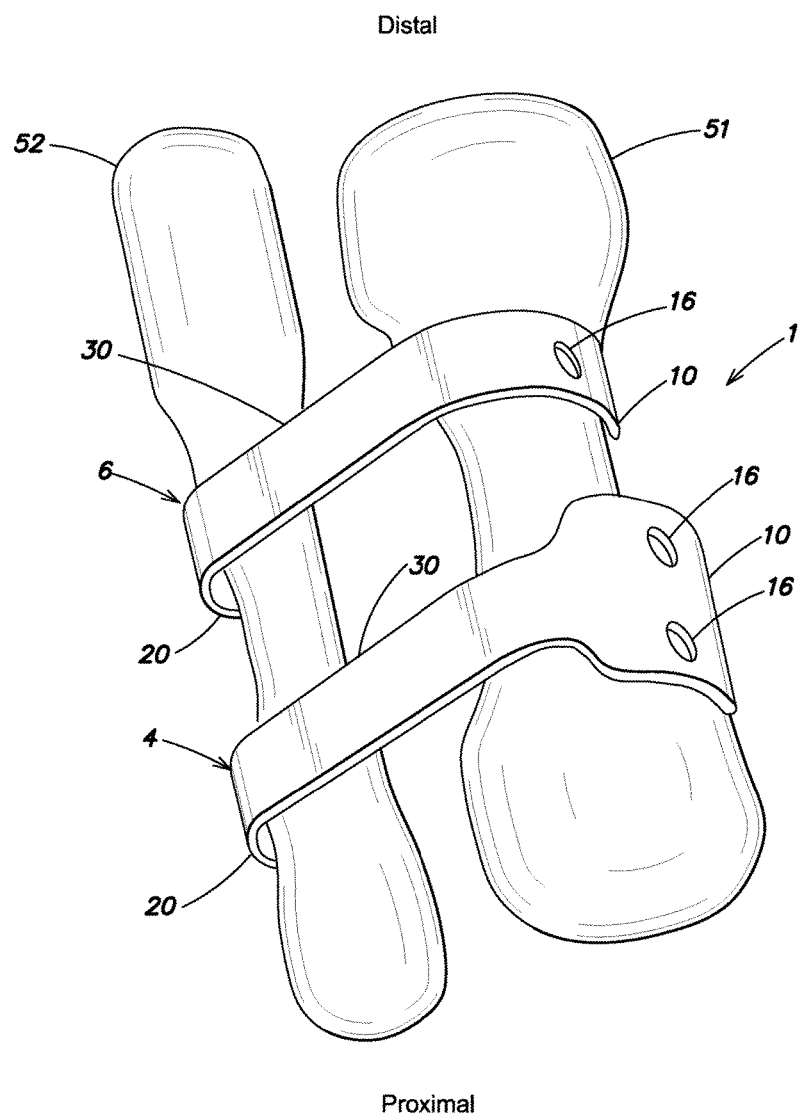
FIG. 3A depicts a top perspective view of first and second metatarsals with an implant system in accordance with an aspect of the invention.
Figure 3B:
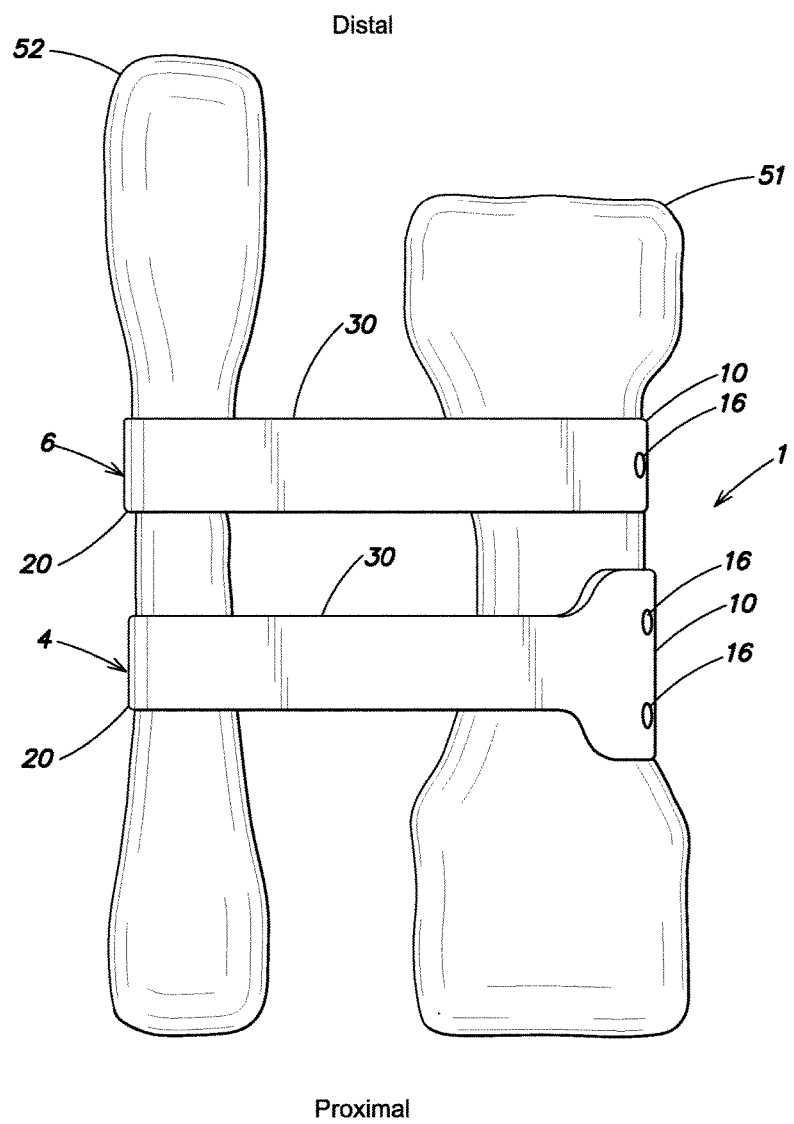
FIG. 3B depicts a top view of FIG. 3A.

According to one aspect, the implant includes one or more features enabling attachment or coupling of the implant to the bone. In this manner, the implant can exert an appropriate hold on the bone to urge it into its correct anatomical position. As shown in FIGS. 3A-B, in one embodiment, implants 4, 6 may include a first bone engaging feature 10 at one end that is constructed in a manner to engage the first metatarsal bone 51, and a second bone engaging feature 20 at the other end that is constructed in a manner to engage the second metatarsal bone 52.

Figure 5:
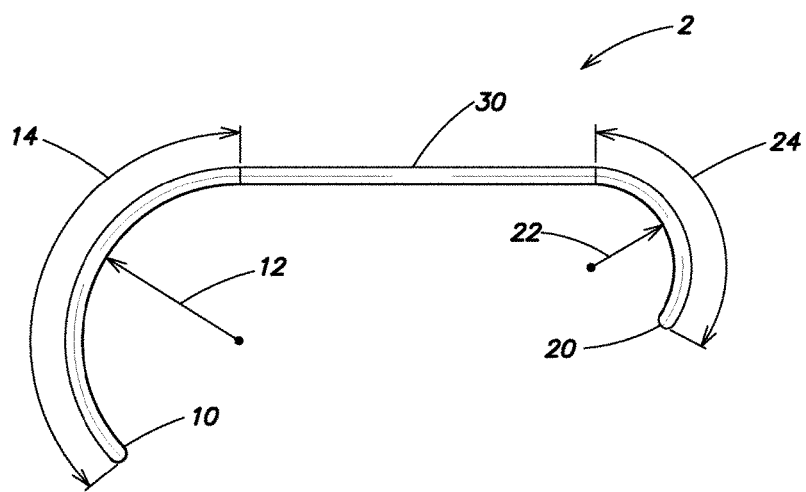
FIG. 5 depicts a side view of the implant of FIG. 4A.
Figure 6:
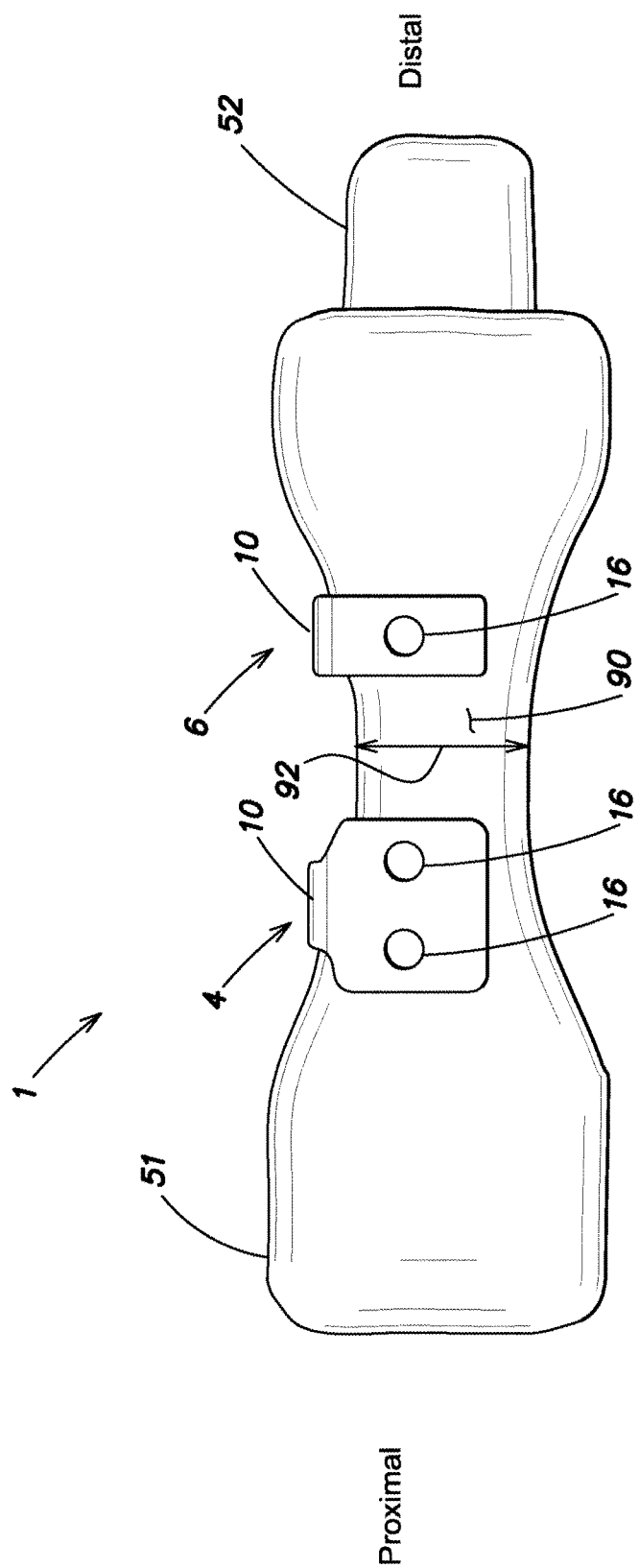
FIG. 6 depicts a medial view of FIG. 3A.
Figure 7A:
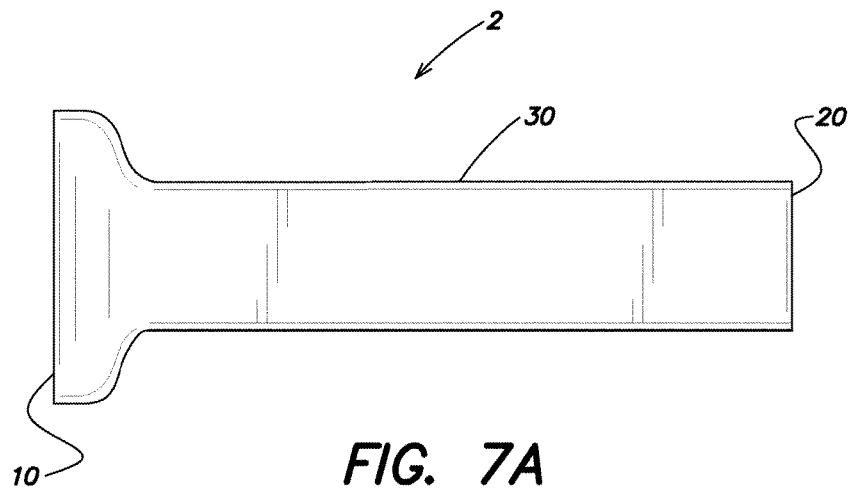
FIG. 7A depicts a top view of the implant of FIG. 4A.
Figure 7B:
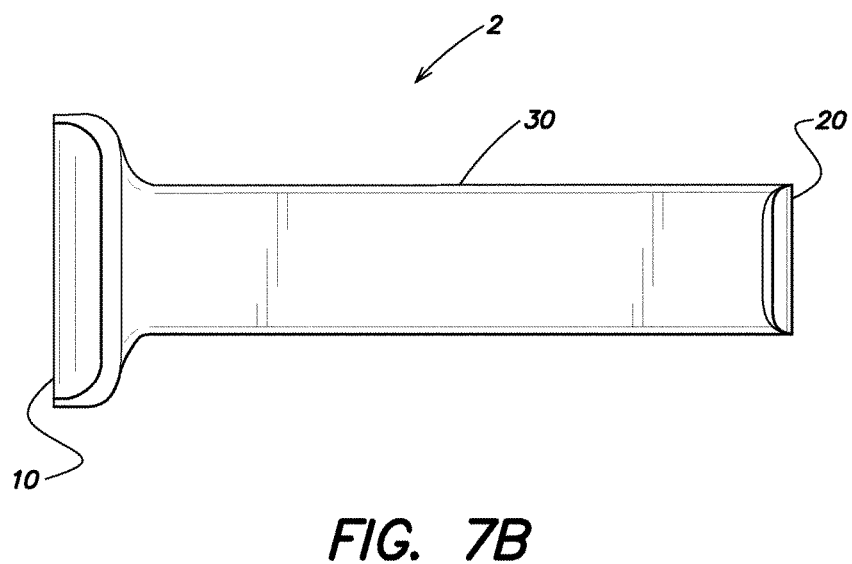
FIG. 7B depicts a bottom view of the implant of FIG. 4A.

In one embodiment, the bone engaging feature is shaped to partially wrap around the bone. In the embodiment shown in FIG. 5, the side profile of implant 2 may form a C-shape to hook on the lateral aspect of a bone. Each bone engaging feature 10, 20 may have a specific radius of curvature and arc length. The radius of curvature and arc length of each bone engaging feature may allow each end of the implant to hook on the lateral aspect of a bone, thereby partially wrapping around the bone. First bone engaging feature 10 has a radius of curvature 12 and arc length 14. Likewise, second bone engaging feature 20 has a radius of curvature 22 and arc length 24. The radius of curvature of each bone engaging feature may range from about 1 mm to 25 mm. The arc length of each bone engaging feature may range from about 1 mm to about 150 mm. As shown in FIG. 3A, first bone engaging feature 10 of the proximal implant 4 hooks on the lateral aspect of the first metatarsal 51 and partially wraps around the first metatarsal 51. Similarly, as shown in FIG. 3B, second bone engaging feature 20 of the proximal implant 4 hooks on the lateral aspect of the second metatarsal 52 and partially wraps around the second metatarsal 52. Depending on its radius of curvature and arc length, the bone engaging feature may partially wrap around bone by extending to a certain dorsal-ventral depth along the lateral aspect of the bone. In some embodiments, as shown in FIG. 6, the first bone engaging feature 10 partially wraps around the first metatarsal 51 by extending down to more than half the dorsal-ventral depth 92 of the lateral aspect 90 of the first metatarsal 51. In some embodiments, a bone engaging feature may partially wrap around bone by extending to slightly more than half the dorsal-ventral depth, half the dorsal-ventral depth, slightly less than half the dorsal-ventral depth, or less than half the dorsal-ventral depth of the lateral aspect of a bone. In some embodiments, the bone engaging features may also be shaped to fit the medial-lateral contours of bone. For example, a distal portion of bone engaging feature 10 may curve inward medially (not shown) to meet the first metatarsal 51. Of course, it should be appreciated that the present invention is not limited in this respect and other suitable shapes may be employed. For example, the bone engaging feature may be formed in a semi-circular shape or otherwise have a longer arc length to wrap further, but still partially, around the bone. In some cases, the bone engaging feature may be arranged to wrap completely around the bone.

According to one aspect, the bone engaging features may be configured to provide a close anatomical fit to the patient such that the distance between the implant and the metatarsals in the ventral-dorsal direction is decreased. Providing a close anatomical fit may help enhance patient comfort. A large distance between the implant and the metatarsals in the ventral-dorsal direction may give rise to a bulky protrusion on the dorsal surface of the foot which may interfere with daily activities and cause discomfort. In addition, a poorly fit implant may be more easily disturbed or dislodged by external forces on the foot. In some embodiments, the radius of curvature and arc length of the bone engaging features may be adjustable to provide a close anatomical fit to the patient. The bone engaging features may be adjusted preoperatively or intraoperatively. A surgeon may bend (manually or with a tool such as a plate bender) each end of the implant to adjust the radius of curvature and/or arc length of the bone engaging features to fit the subject's anatomy. In some embodiments, the bone engaging features may also be adjusted to fit the medial-lateral contours of bone by bending the bone engaging features in the medial or lateral direction. In another embodiment, bone engaging features may include heat-shrinkable components. In yet another embodiment, bone engaging features may include multiple segments that can be removed or added to in order to alter the radius of curvature and/or arc length. In other embodiments, the radius of curvature and arc length may be permanent, and a surgeon may choose from a set of implants with different discrete curvatures and arc lengths to best suit the subject's anatomy.

In some embodiments, the implant may include other types of bone engaging features such as anchor holes. Anchoring elements may be passed through the anchor holes and fixed into the bone, thereby anchoring the implant to the bone. Anchoring elements include bone screws, surgical screws, orthopedic screws, barbs, and other suitable hardware, as this aspect is not limited in this regard. In addition, screws may be of the locking or non-locking type, as this aspect is not limited in this regard.

In some embodiments, the implant may include other types of or additional bone engaging features that enhances attachment of the implant to the bone. Other types of bone engaging features may include bonding or cementation that adheres the implant to the bone. Such bonding or cementation may be applied at any contacting interface between the implant and the bones.

Figure 9:
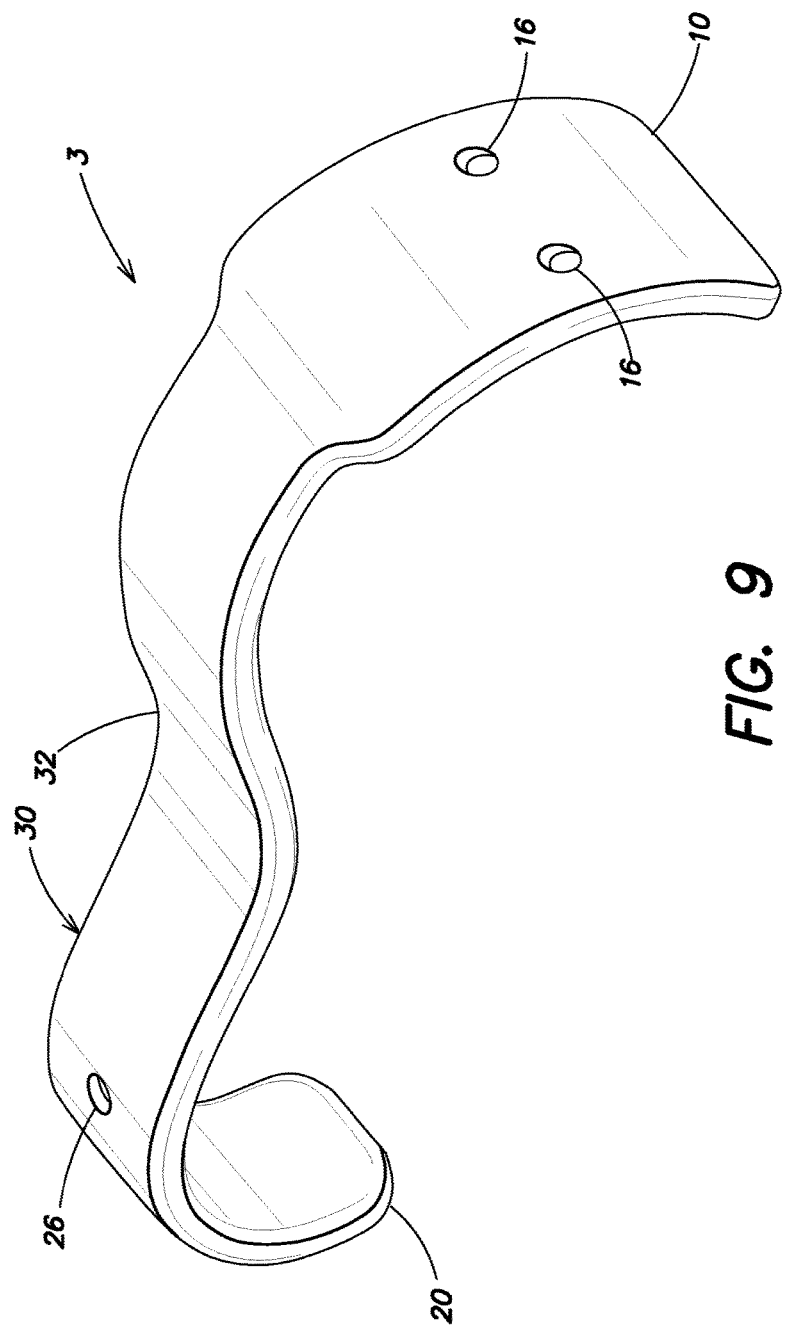
FIG. 9 depicts one embodiment of an implant including a curvature on the intermediate portion.

Bone engaging features disclosed in the above mentioned embodiments may be combined or separated, as the invention is not limited in this regard. For example, FIGS. 3A-3B illustrate an embodiment in which bone engaging features 10, 20 include a rounded shape that permits the end of the implant to wrap around the bone, combined with bone anchor holes 16, which also promote engagement between the implant to bone. Bone anchor holes may be positioned anywhere along the implant. As illustrated in FIG. 9, in some embodiments, an implant 3 may have an intermediate portion 30 that includes a dorsal bone anchor hole 26.

Figure 10:
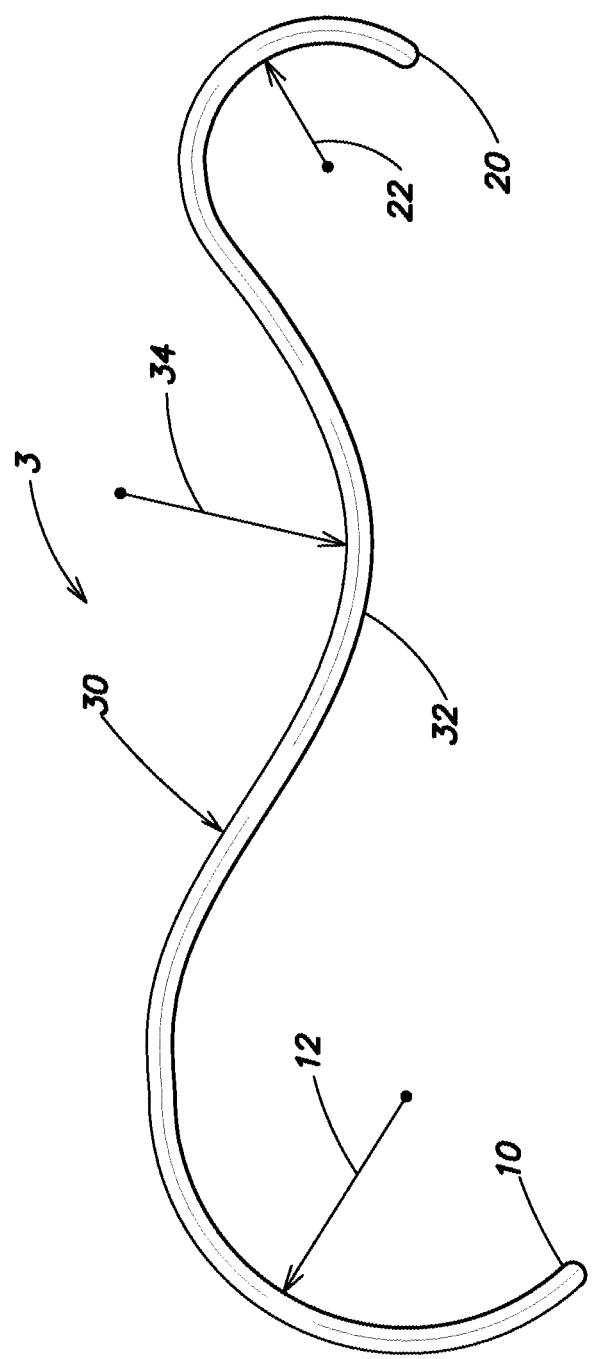
FIG. 10 depicts a side view of the implant of FIG. 9.
Figure 11A:
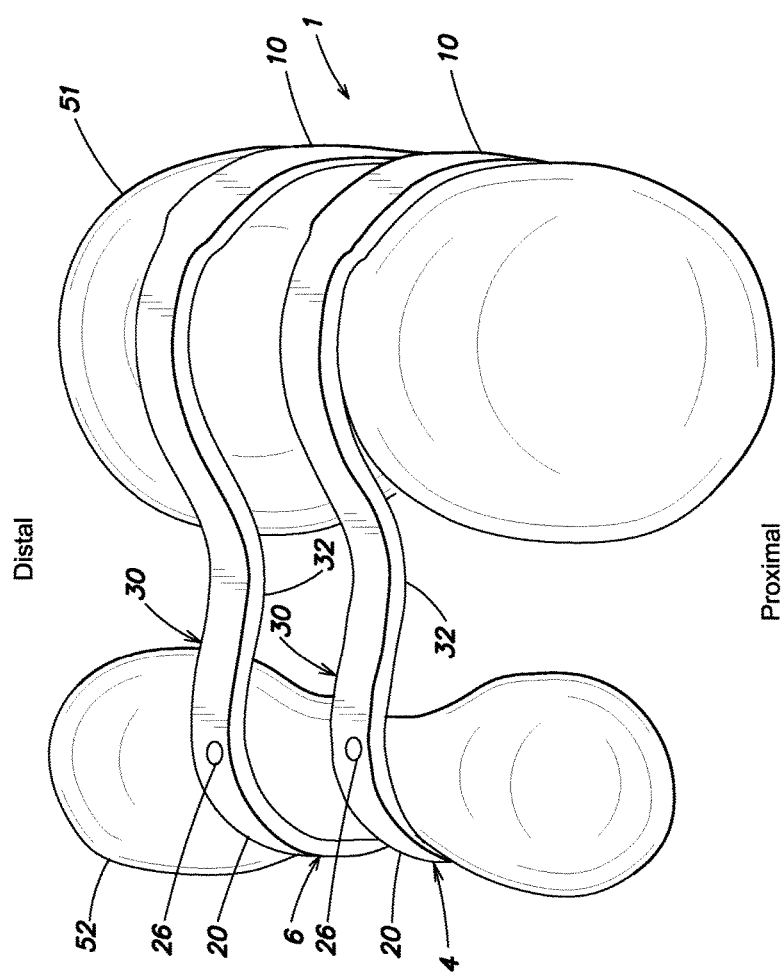
FIG. 11A depicts a top perspective view of first and second metatarsals with an implant system in accordance with an aspect of the invention.
Figure 11B:
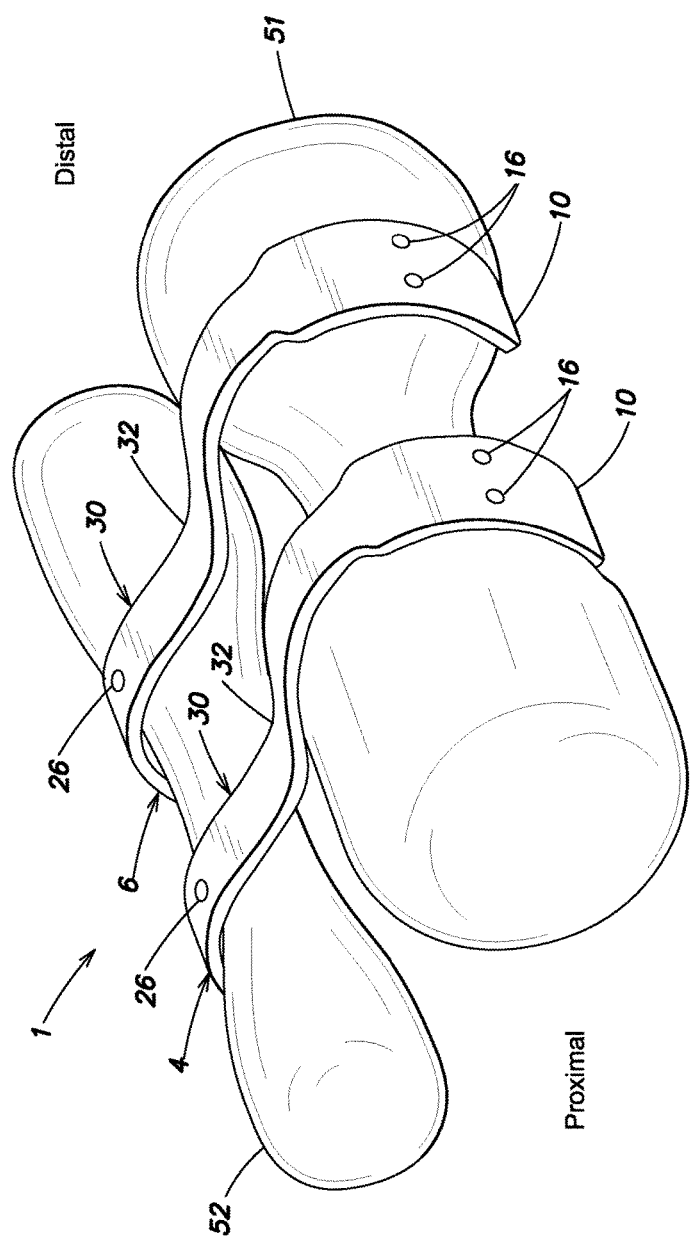
FIG. 11B depicts another top perspective view of FIG. 11A.

As can be appreciated, the implant exerts an appropriate tension force between the metatarsals to draw the first toward the second metatarsal, urging the improperly positioned metatarsal back toward its correct anatomical position. In one embodiment, as shown in FIGS. 4A-B and 7A-B, the implant includes an intermediate portion 30 connecting the first 10 and second 20 bone engaging features. In this particular embodiment, the intermediate portion has a substantially flat profile. In some embodiments, in order to improve the anatomical fit of the implant, the intermediate portion may include a curvature. As shown in FIGS. 9-10, intermediate portion 30 of implant 3 includes a curvature 32. The curvature may be positioned such that, when the implant is engaged with the metatarsals, the curvature is positioned between the metatarsals. This curvature may allow the implant to be positioned closer to the metatarsals in the ventral-dorsal direction, thereby reducing the ventral-dorsal distance from the implant to the bones. FIGS. 11A-B depict one embodiment in which intermediate portion 30 includes a curvature 32 positioned between the first 51 and second 52 metatarsals.

In some embodiments, the implant may include areas of surface roughness or other suitable features or materials that encourage ingrowth of tissue into the implant to help the integration of the implant into the body. Alternatively or in addition, the implant may include certain features and/or materials in desired locations that resist tissue attachments to help prevent immobilization.

The tissue ingrowth features and/or materials may help to encourage ingrowth of soft tissue and/or bone into the implant. In some embodiments, tissue ingrowth features and/or materials may be located on the dorsal side of the implant, the plantar side of the implant, or both. Alternatively or in addition, tissue ingrowth features and/or materials may be located at any one of or at any combination of the other edges of the implant.

In some embodiments, the implant may include a combination of tissue ingrowth features and/or materials, as well as features and/or materials that resist tissue attachments. In some embodiments, one side of the implant (plantar side or dorsal side) may include features and/or materials that promotes tissue ingrowth, while the other side of the implant may include features and/or materials that resists tissue attachments. In some cases, features and/or materials that resist tissue attachments may be located at any one of or at any combination of the other edges of the implant.

Examples of possible surface treatments for promotion of tissue ingrowth include, but are not limited to: plasma etching, sand blasting, machining and other treatments to roughen the surface or otherwise provide a suitable surface texture.

In some embodiments, the implant may include a layer of mesh fabric that promotes tissue ingrowth. The mesh may be embedded into the implant or attached to the implant by any suitable means, including tying, sutures, clips, adhesives, heat bonding, or solvent bonding. The mesh may be formed of a sheet of knitted polypropylene monofilament mesh fabric such as MARLEX mesh. When implanted, the polypropylene mesh stimulates an inflammatory reaction which promotes rapid tissue ingrowth into and around the mesh structure. Alternatively, other surgical materials which are suitable for tissue ingrowth may be utilized including PROLENE, MERSELENE, DACRON, TEFLON textile based meshes, microporous polypropylene sheeting (CELGARD), and expanded PTFE (GORETEX). Absorbable meshes, including polyglactin (VICRYL) and polyglycolic acid (DEXON), may be utilized as well. It also is contemplated that the mesh fabric may be formed from monofilament or multifilament yarns and that woven, molded and other recognized methods of forming prosthetic mesh materials would be suitable.

Examples of possible features and/or materials that resist tissue attachments may include, but are not limited to: a smooth surface finish with little to no surface roughness, a mesh material with small pore sizes that do not encourage tissue ingrowth, nonporous materials, hydrophobic materials, and other treatments or materials to resist tissue attachments.

Figure 4A:
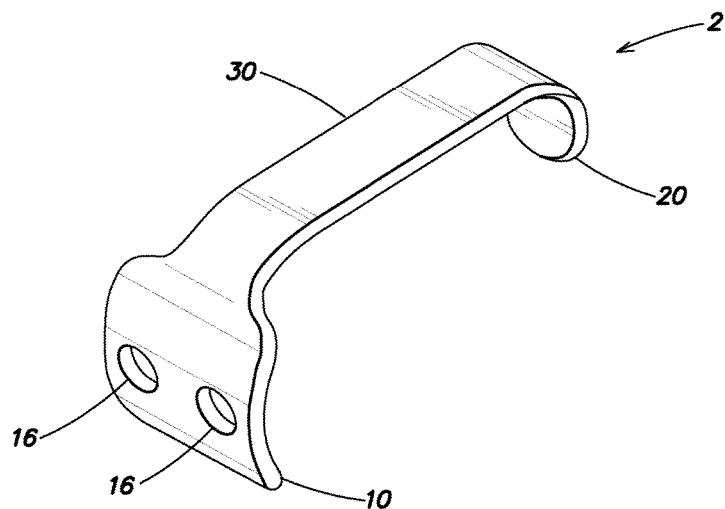
FIG. 4A depicts a top perspective view of one embodiment of an implant.
Figure 4B:
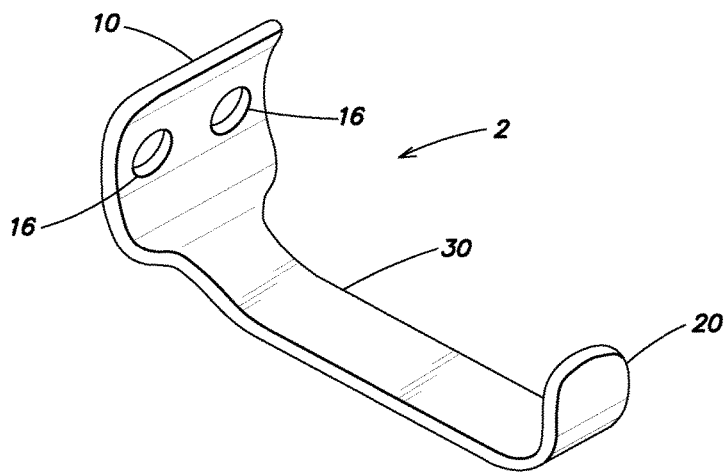
FIG. 4B depicts an underside perspective view of the implant of FIG. 4A.
Figure 4C:
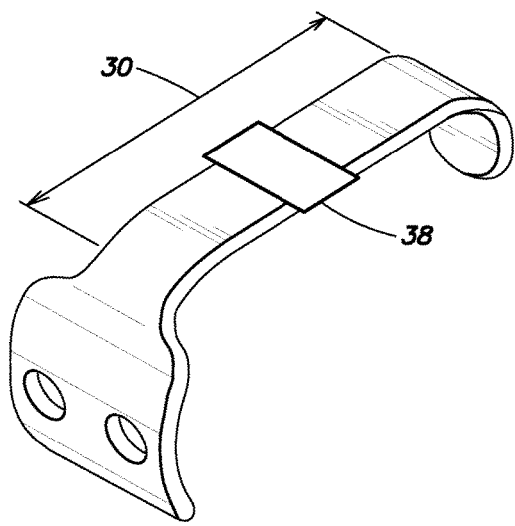
FIG. 4C depicts an implant with an adjustable section.
Figure 4D:
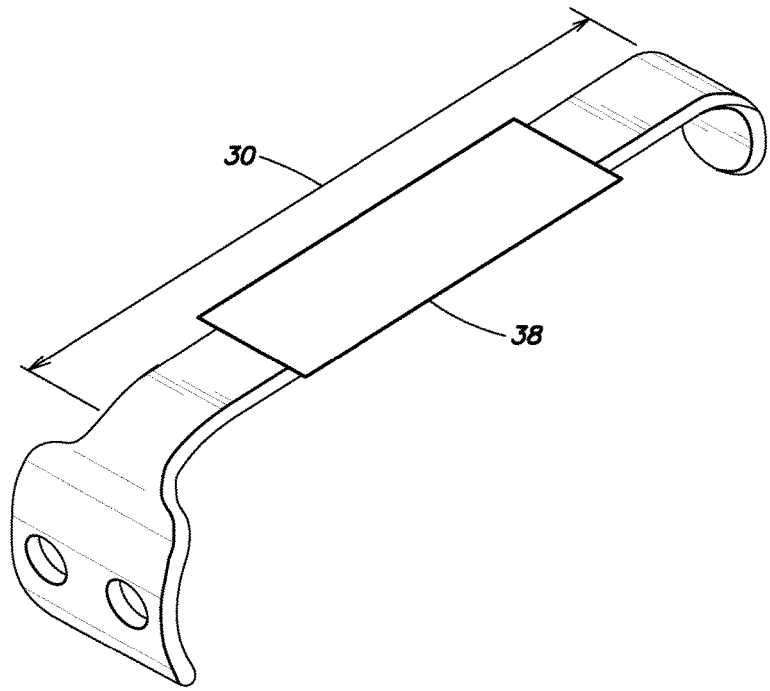
FIG. 4D depicts the implant of FIG. 4C with an expanded adjustable section.

According to one aspect, the intermediate portion may be adjustable to enhance the anatomical fit of the implant. In some embodiments, the intermediate portion may have an adjustable length, width, and/or cuvature. For example, the intermediate portion may include heat shrinkable components, slidably adjustable components, and/or bendable components that permit a user to adjust the length, width, and/or curvature of the intermediate portion. For example, FIGS. 4C-D shows schematics of an implant with an adjustable section 38 that expands from a shorter length in FIG. 4C to a longer length in FIG. 4D, thereby increasing the overall length of the intermediate portion 30. In one embodiment, the adjustable section may comprise one or more struts that may be length-adjustable, such as a turnbuckle-like device. In another embodiment, the adjustable section may comprise multiple telescoping segments such that the intermediate portion can be expanded or compressed to various lengths. In yet another embodiment, adjustable section may include multiple removable segments. Segments may be added or removed to increase or decrease the length of the adjustable section. In another embodiment, the adjustable section may comprise two segments that can be interlocked with one another at multiple positions to enable a range of intermediate portion lengths. For example, the first segment may have a series of slots arranged linearly along the length of the first segment. The second segment may have a series of tabs arranged linearly along the length of the second segment. The tabs on the second segment may be sized to be able to slide into the slots on the first segment. The tabs and slots may be arranged such that engagement between the tabs and slots locks the tabs in place, e.g., by shaping tabs into a hooked configuration that can hook onto the slots, by interference fit between the tabs and the slots, or by other suitable arrangement. The length of the intermediate portion is adjusted by sliding the two portions relative to one another and changing the amount of overlap between the two portions. A maximum amount of overlap between the two portions enables a minimum intermediate portion length, while a minimum amount of overlap between the two portions enables a maximum intermediate portion length. The adjustable section may span the entire length and width of the intermediate portion, or the adjustable section may be only one section of the intermediate portion. In addition, the intermediate portion may be bendable, either by hand or with a tool such as a plate bender, to create a curvature suitable to the patient's anatomy. The intermediate portion may be adjusted preoperatively or intraoperatively.

According to one aspect, the intermediate portion may be located on only one side of the bone. In some embodiments, where the implant is used in a foot, the intermediate portion may be located only dorsal to the metatarsals, such that the intermediate portion is positioned above the metatarsals, as opposed to between the metatarsals or below the metatarsals. Such an arrangement may provide increased patient comfort and may require a less invasive implantation procedure.

Figure 11C:
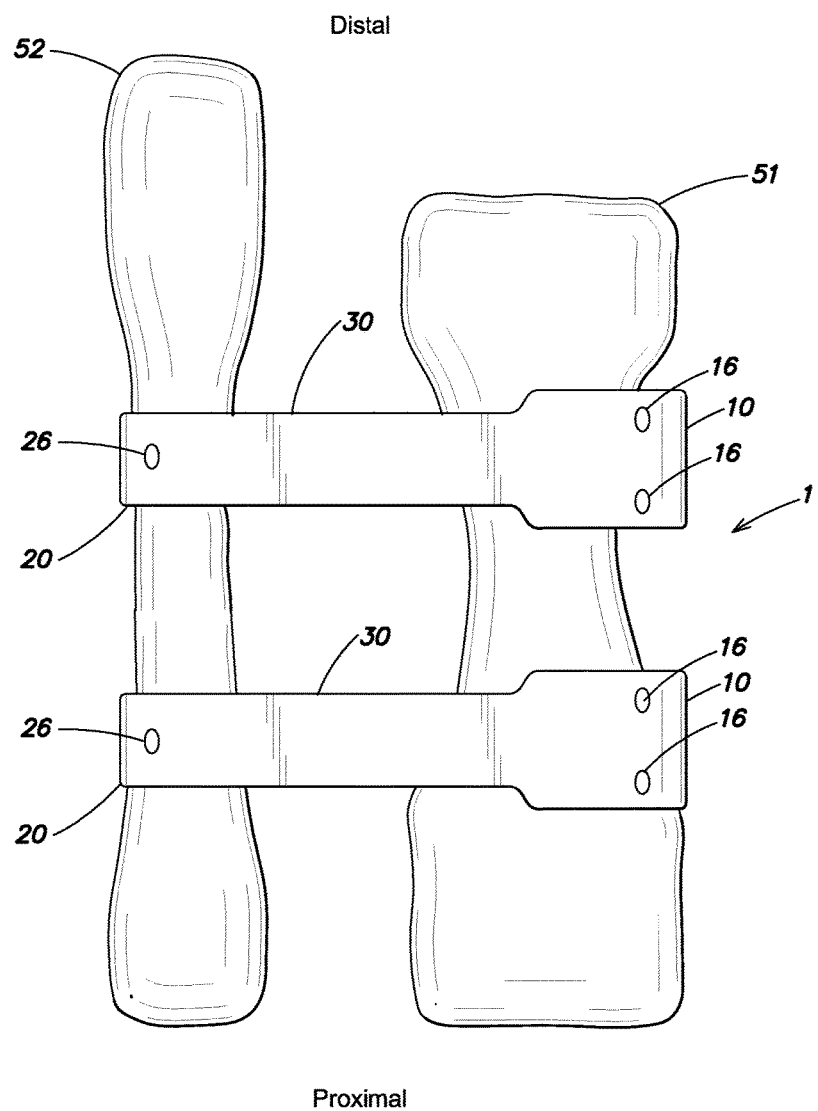
FIG. 11C depicts a top view of FIG. 11A.

According to another aspect, the intermediate portion may contact bone. In some embodiments, the intermediate portion may contact the dorsal aspect of the metatarsals. In some embodiments, the intermediate portion may include at least one bone anchor hole arranged to accept an anchoring element that anchors the implant to the bone. As shown in FIGS. 11A-C, dorsal bone anchor hole 26 is arranged to accept an anchoring element that anchors the implant to the dorsal aspect of the second metatarsal 52. In some embodiments, the intermediate portion may include surface roughness or other suitable feature that encourages ingrowth of tissue into the intermediate portion to help hold the implant in place.

According to one aspect, the width of the implant in the distal-proximal direction is configured to provide a sufficient surface area of contact between the implant and the bone. A larger surface area of contact may permit the implant to better attach to the bone. In some instances, a wider distal-proximal width may permit an increased number of anchoring elements to fit on the implant. On the other hand, the width of the implant may be limited by the anatomy of the patient and by considerations of invasiveness and comfort. For example, wider implants may require more extensive incisions during implantation and may hinder movement of the foot. Arrangements may be selected depending on the patient's anatomy. For example, if there is sufficient surface area on the bone at the implantation site, an enlarged bone engaging feature may be used. In some embodiments, the width of the implant in the distal-proximal direction may be uniform. For example, as shown in FIGS. 3A-B, distal implant 6 has a constant distal-proximal width throughout the entire length of the device. The first bone engaging feature 10, second bone engaging feature 20, and intermediate portion 30 of distal implant 6 all have the same width.

Figure 8:
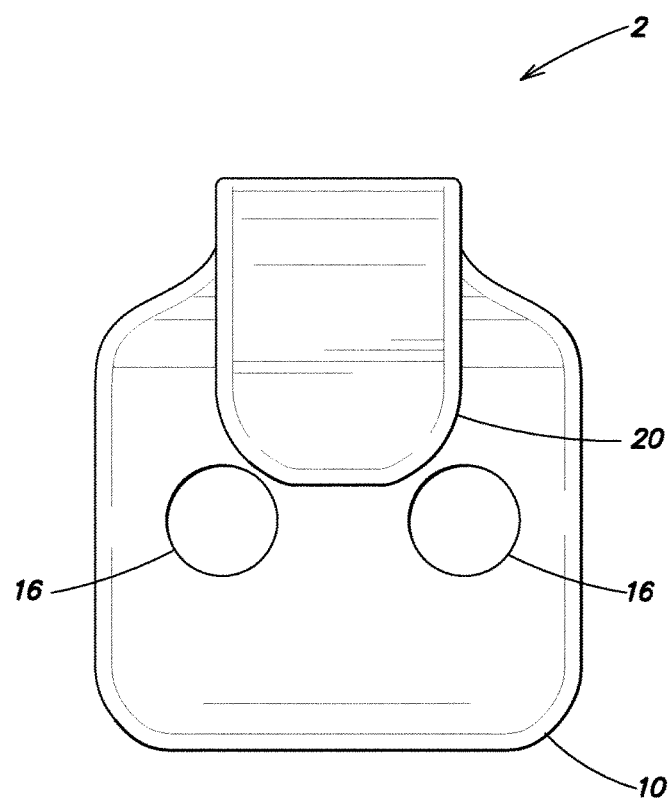
FIG. 8 depicts a lateral view of the implant of FIG. 4A.

In other embodiments, the distal-proximal width of the implant may be non-uniform. For example, as shown in FIGS. 3A-B, proximal implant 4 has an enlarged first bone engaging feature 10, such that the distal-proximal width at the first bone engaging feature 10 is wider than the intermediate portion 30 and the second bone engaging feature 20. Similarly, in FIGS. 7-8, implant 2 has an enlarged first bone engaging feature 10 such that the distal-proximal width at the first bone engaging feature 10 is wider than the intermediate portion 30 and the second bone engaging feature 20. In addition, FIGS. 3A-B also show that the distal-proximal width of proximal implant 4 steps down from a wider width at first bone engaging feature 10 to a more narrow width that is uniform from the intermediate portion 30 to the second bone engaging feature 20. Of course, it should be appreciated that the present invention is not limited in this respect and other arrangements may be employed. In one embodiment, the proximal implant may have a constant distal-proximal width, while the distal implant may have an enlarged first and/or second bone engaging feature. In another embodiment, the distal implant may have a constant distal-proximal width, while the distal implant may have an enlarged first and/or second bone engaging feature. In another embodiment, the distal and proximal implants may both have constant distal-proximal widths. In yet another embodiment, the distal and proximal implants may both have enlarged first and/or second bone engaging features. In yet another embodiment, the first bone engaging feature, the second bone engaging feature, and the intermediate portion may all have different distal-proximal widths from one another.

The implant is implanted into the body of a patient according to various aspects of the invention. In the case of treating hallux valgus or tailor's bunion, a surgical procedure is required for implantation of the implant. Prior to surgery, images may be taken of the implantation site and anatomical measurements may be made. Images may include X-Rays, Magnetic Resonance Imaging (MRI), Computed Tomography (CT) scans, or other suitable images. Anatomical measurements may include the intermetatarsal angle (the interior angle between the first and second metatarsals for hallux valgus or the interior angle between the fourth and fifth metatarsals for tailor's bunion), the distance between the first and second metatarsophalangeal (MTP) joints for hallux valgus (fourth and fifth MTP joints for tailor's bunion), curvature of the metatarsals, etc. Based on the images and anatomical measurements, a suitable-sized implant is chosen. Depending on the anatomy of the patient, the implant may be used as a proximal implant or a distal implant. As shown in FIGS. 3A-B, an implant system 1 may include both a proximal implant 4 and a distal implant 6.

In some embodiments, an implant system composed of multiple implants may be used. In some cases, the use of multiple implants may depend on the patient's intermetatarsal angle. In general, a normal intermetatarsal angle is less than about 9 degrees. In some embodiments, if the subject's intermetatarsal angle is less than about 12 degrees, a single implant may be sufficient. In some embodiments, if the subject's intermetatarsal angle is over about 12 degrees, two implants may be used. As shown in FIGS. 2, 3, and 11, a first implant 4 may be implanted at a proximal location and a second implant 6 may be implanted at a distal location. Of course, it should be appreciated that the present invention is not limited in this respect and other implantation positions may be used. For example, the first and second implants may be implanted closer or further away from each other. First implant 4 may sit at a position more or less proximally than that shown in FIGS. 3A-B, and the second implant 6 may sit at a position more or less distally than that shown in FIGS. 3A-B.

According to one aspect, first and second implants may be connected together to form a double-construct implant. For example, the double-construct implant may include a connector or section that joins first and second implants together. The connector may be arranged to be positioned in the space between the metatarsals upon implantation such that the double-construct implant forms an H-shape configuration. Alternatively, in some embodiments, the connector joining the first and second implants may be a plate that is wider than the space between the metatarsals. In another embodiment, the double-construct implant may have multiple connectors that join the first and second implants together. First and second implants may be connected together in any suitable way to form a double-construct implant, as this aspect is not limited in this regard. In some embodiments, the connector or connectors may be adjustable to enhance the anatomical fit of the implant. In some embodiments, the connector may have an adjustable length and/or thickness. For example, the connector may include heat shrinkable components, slidably or rotatably adjustable components, and/or bendable components that permit a user to adjust the length, width, and/or curvature of the connector. In another embodiment, the connector may include multiple removable segments. Segments may be added or removed to increase or decrease the length of the connector. In addition, the connector may be bendable, either by hand or with a tool such as a plate bender, to create a curvature suitable to the patient's anatomy. The connector may be adjusted preoperatively or intraoperatively.

According to certain aspects of the invention, a surgical procedure is used to deploy the implant. In some embodiments, when treating a patient with hallux valgus, a standard medial approach for hallux valgus repair may be employed. During the procedure, the surgeon may perform a complete lateral release either through a separate distal approach or through the medial incision. A small incision may be placed just lateral to the second metatarsal, thereby exposing the metatarsal. A fascial elevator may be inserted from the medial aspect of the first metatarsal just proximal to the metaphysis, extending to the lateral aspect of the second metatarsal. As a result, the soft tissue may be elevated to form an envelope. The surgeon may then choose an appropriately sized implant based on the patient's anatomical characteristics. The implant may be inserted into the space provided by the fascial elevator, and may be placed around the second metatarsal. The first metatarsal may then be manually reduced, and the implant may be secured to the first metatarsal with locking or non-locking bone screws or other suitable bone engaging feature. Bone screws or other hardware may be drilled just through the cortex of the bone to a depth of about 1 mm, without fully penetrating through the entire bone. As illustrated in FIGS. 3 and 9, in one embodiment, bone screws or other hardware may be inserted though bone anchor holes 16. An additional screw may be secured dorsally into the second metatarsal. As illustrated in FIG. 9, in one embodiment, the additional screw may be inserted through dorsal bone anchor hole 26. In some embodiments, treatment of tailor's bunion may employ a similar procedure. Of course, it should be appreciated that the present invention is not limited in this respect and other suitable procedures may be employed.

According to one aspect, the implant may be positioned on the dorsal side of the metatarsal bones. Alternatively, the implant may be positioned on the ventral side of the metatarsals. Positioning of the implant on the dorsal side of the metatarsals may be preferred due to improved patient comfort and less interference with daily activities. In addition, deployment of the implant on the dorsal side of the metatarsals may require a less invasive surgical procedure.

According to one aspect, depending on the extent of the deformity (e.g. large intermetatarsal angle), the implant may be used as an adjunctive device in combination with an additional surgical procedure. Surgical procedures include wedge osteotomy, transpositional osteotomy, fusion, joint replacement, or other suitable surgical procedure, as this aspect is not limited in this regard.

Figure 13:
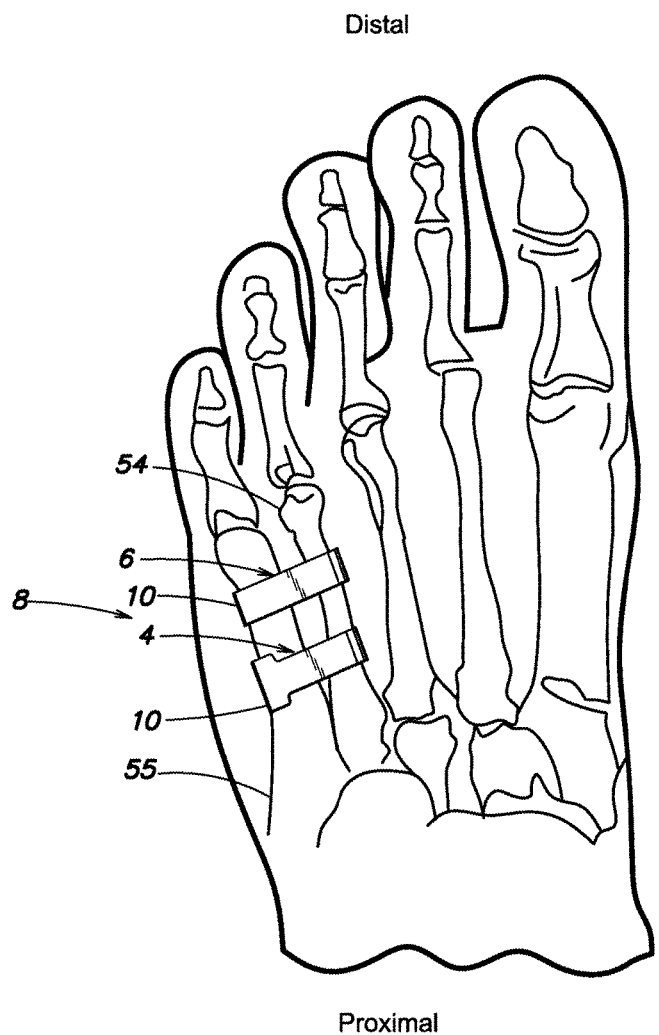
FIG. 13 depicts a corrected foot with an implant system positioned on the fourth and fifth metatarsals in accordance with an aspect of the invention.

According to one aspect, the implant is not limited to use with the first and second metatarsals. In some embodiments, the implant may be used to treat a condition called tailor's bunion, also known as a bunionette. As shown in FIG. 13, implant system 8, including proximal implant 4 and distal implant 6, may stabilize the fifth metatarsal 55 to the fourth metatarsal 54 in the same manner that the first metatarsal 51 is stabilized to the second metatarsal 52 in the treatment of hallux valgus (FIGS. 2-3). Although FIG. 13 depicts a proximal implant 4 with an enlarged first bone engaging feature 10, and a distal implant 6 with a uniform proximal-distal width, it should be appreciated that this aspect is not limited in this regard. In one embodiment, proximal implant 4 may have a uniform proximal-distal width, and distal implant 6 may have an enlarged first and/or second bone engaging feature. In another embodiment, distal implant 6 may have a uniform proximal-distal width, and proximal implant 4 may have an enlarged first and/or second bone engaging feature. In yet another embodiment, both implants 4,6 may have uniform proximal-distal widths. In other embodiments, a single implant or a double-construct implant may be used. Any arrangement suitable to fit the patient's anatomy may be used, as this aspect is not limited in this regard.

In some embodiments, the implant may remain permanently within the body. In some cases, the implant may be replaced after a certain amount of time. In others, the implant may be bioabsorbable or may be removed after a certain amount of time.

In some embodiments, the implant may be constructed of any biocompatible material such as titanium, nickel, nickel titanium alloy, nitinol or other shape-memory alloy, silver, gold, plastic, or other suitable material. In some embodiments, the material may be substantially rigid, as opposed to elastic. In other embodiments, the material may be elastic. In some cases, the material may be substantially deformable by hand. The implant may be formed from a plate or strip of material that is about 0.7 to about 1.2 millimeters thick and about 5 to about 15 millimeters wide.

According to one aspect, the implant may be formed using any suitable process. The implant may be stamped out of sheet metal or cast from metal and curved at each end by a plate bender or other suitable tool. Any suitable finishing and/or sterilization processes may be applied to the implant, as this aspect is not limited in this regard.

According to one aspect, the implant may have permanent discrete lengths, widths and/or thicknesses. In some embodiments, a range of implants of different sizes may be provided in a kit. For example, in one embodiment, the kit may include a range of five discretely sized implants or implant systems: the first may be suitable for very small patients, the second may be suitable for patients who are somewhat smaller than average, the third may be suitable for average-sized patients, and so on, where the size range of implants or implant systems is linearly scaled. In some embodiments, the first implant may have a length of about 32 mm, the second may have a length of about 34 mm, the third implant may have a length of about 36 mm, the fourth implant may have a length of about 38 mm, and the fifth implant may have a length of about 40 mm. In some embodiments, kits may be designed to suit a specific gender, age, and/or severity of deformity. For example, kits for pediatric applications may include smaller implants than kits for adult applications. In some embodiments, kits may also include instruments used to adjust the implants, such as a plate bender. Of course, it should be appreciated that the present invention is not limited in this respect and other suitable kits may be employed. For example, the kits may include any number of implants at any range of sizes. In another embodiment, each discretely-sized implant may be provided individually rather than in a collective kit.

The above aspects may be employed in any suitable combination, as the present invention is not limited in this respect. Also, any or all of the above aspects may be employed in an implant; however, the present invention is not limited in this respect, as the above aspects may be employed with other medical devices.

Also, as described herein, the surgical implant may be used for correction of hallux valgus or tailor's bunion. However, embodiments of the invention are not limited to use for correction of hallux valgus, tailor's bunion, or deformities of the foot bones. According to some aspects, the surgical implant may be used in other locations of the body, for example, with the metacarpals of the hand, the radius and ulna of the arm, or the fibula and tibia of the leg, etc., as aspects are not limited in this regard. In addition, while some embodiments of the invention disclosed herein may discuss use of a surgical implant with a human subject, the surgical implant may be used in non-human subjects as well, as the invention is not limited in this regard.

Having thus described several aspects of at least one embodiment of this invention, it is to be appreciated various alterations, modifications, and improvements will readily occur to those skilled in the art. For example, the surgical implant described herein may be adapted for placement in other locations. Such alterations, modification, and improvements are intended to be part of this disclosure, and are intended to be within the spirit and scope of the invention. Accordingly, the foregoing description and drawings are by way of example only.

What is claimed is:

1. An implant for repositioning bones of a patient to a more anatomically correct position, the implant comprising:
   a first bone engaging feature with a first outer surface and a first bone contacting surface opposing the first outer surface configured to wrap partially around a first bone and defining a first free end of the implant;
   a second bone engaging feature with a second outer surface and a second bone contacting surface opposing the second outer surface configured to wrap partially around a second bone and defining a second free end of the implant; and
   an intermediate portion extending between and connecting the first and second bone engaging features and defining an intermediate outer surface and an intermediate inner surface opposing the intermediate outer surface, the intermediate portion and the bone engaging features cooperating to enable the first bone to be drawn toward the second bone,
   wherein the first bone contacting surface includes a first tip at the first free end of the first bone engaging feature that is wider than a maximum width of the intermediate portion,
   wherein the second bone contacting surface includes a second tip at the second free end of the second bone engaging feature that is at least as wide as the maximum width of the intermediate portion,
   wherein the first bone contacting surface of the first bone engaging feature has a first height, the second bone contacting surface of the second bone engaging feature has a second height, and the first height is larger than the second height,
   wherein an entirety of the intermediate outer surface of the intermediate portion is positioned at the same height as a first point where the first bone engaging feature couples to the intermediate portion and a second point where the second bone engaging feature couples to the intermediate portion.

2. The implant of claim 1, wherein at least one of the first and second bone engaging features further includes at least one bone anchor hole configured to accept an anchoring element that anchors the implant to bone, and wherein the at least one bone anchor hole is positioned on a curved portion of at least one of the first and second bone engaging features.

3. The implant of claim 1, wherein the intermediate portion includes at least one bone anchor hole.

4. The implant of claim 1, wherein the implant is substantially rigid.

5. The implant of claim 1, wherein the intermediate portion is arranged such that, when the implant is engaged with the first and second bones, the intermediate portion is positioned only dorsal to metatarsals of a foot of a patient.

6. The implant of claim 1, wherein the first bone engaging feature has a first radius of curvature and the second bone engaging feature has a second radius of curvature that is smaller than the first radius of curvature.

7. The implant of claim 1, wherein the first bone engaging feature has a first arc length and the second bone engaging feature has a second arc length that is smaller than the first arc length.

8. The implant of claim 1, wherein the first and second bone engaging features are configured to engage metatarsals of a patient's foot and are configured to decrease an inter-metatarsal angle between the metatarsals.

9. The implant of claim 1, wherein the implant is used to treat hallux valgus or tailor's bunion.

10. A kit containing multiple sizes of the implant of claim 1.

11. The implant of claim 1, wherein the entirety of intermediate portion is planar.

12. The implant of claim 1, wherein the second bone contacting surface of the second bone engaging feature has the same width as the maximum width of the intermediate portion.

13. An implant for repositioning bones of a patient to a more anatomically correct position, the implant comprising:
   a first bone engaging feature with a first outer surface and a first bone contacting surface opposing the first outer surface configured to wrap partially around and engage a first bone and defining a first free end of the implant;
   a second bone engaging feature with a second outer surface and a second bone contacting surface opposing the second outer surface configured to wrap partially around and engage a second bone and defining a second free end of the implant; and an intermediate portion extending between and connecting the first and second bone engaging features and defining an intermediate outer surface and an intermediate inner surface opposing the intermediate outer surface, the intermediate portion and the bone engaging features cooperating to enable the first bone to be drawn toward the second bone, wherein the intermediate portion is arranged such that, when the implant is engaged with the first and second bones, the intermediate portion is located only dorsal to metatarsals of a foot of a patient, wherein the first bone contacting surface at the first free end of the first bone engaging feature is wider than a maximum width of the intermediate portion, and the second bone contacting surface at the second free end of the second bone engaging feature is at least as wide as the maximum width of the intermediate portion, wherein an entirety of the intermediate outer surface of the intermediate portion is positioned at the same height as a first point where the first bone engaging feature couples to the intermediate portion and a second point where the second bone engaging feature couples to the intermediate portion, and wherein the at least one bone anchor hole is positioned on a curved portion of at least one of the first and second bone engaging features.

14. The implant of claim 13, wherein the first and second bone engaging features are configured to engage to metatarsals of a patient's foot and are configured to decrease an intermetatarsal angle between the metatarsals.

15. The implant of claim 13, wherein the implant is substantially rigid.

16. The implant of claim 13, wherein the intermediate portion is planar.

17. The implant of claim 13, wherein the second bone contacting surface at the second free end of the second bone engaging feature has the same width as the maximum width of the intermediate portion.

18. The implant of claim 13, wherein the first bone contacting surface of the first bone engaging feature has a first height, the second bone contacting surface of the second bone engaging feature has a second height, and the first height is larger than the second height.

* * * * *